United States Patent [19]

Franzmann et al.

[11] 4,271,269

[45] Jun. 2, 1981

[54] REGENERATION OF AN ENZYME IMMOBILIZATE

[75] Inventors: Giselher Franzmann, Witten; Hans-Leo Hülsmann, Wetter, both of Fed. Rep. of Germany

[73] Assignee: Dynamit Nobel Aktiengesellschaft, Troisdorf, Fed. Rep. of Germany

[21] Appl. No.: 39,482

[22] Filed: May 15, 1979

[30] Foreign Application Priority Data

May 19, 1978 [DE] Fed. Rep. of Germany ....... 2821890

[51] Int. Cl.³ .............................................. C12N 11/14
[52] U.S. Cl. .................................... 435/176; 435/106; 435/174
[58] Field of Search ................ 435/174, 176, 181, 106

[56] References Cited

U.S. PATENT DOCUMENTS 3,519,538   7/1970   Messing et al. .................... 435/176

OTHER PUBLICATIONS

Tosz et al., Studies on Continuous Enzyme Reactions, Agr. Biol. Chem., vol. 33, No. 7, 1969, (pp. 1053–1059).
Messing, R. A., Immobilized Enzymes for Industrial Reactors, Academic Press, N.Y., 1975, (pp. 79–95).
Zaborsky, O., Immobilized Enzymes, CRC Press, Cleveland, Ohio, 1973, (pp. 75–82).

*Primary Examiner*—David M. Naff
*Attorney, Agent, or Firm*—Sprung, Felfe, Horn, Lynch & Kramer

[57] ABSTRACT

An enzyme immobilizate comprising an amorphous siliceous support to which an enzyme is bonded by adsorption via an amino alkoxy silane is regenerated after the enzyme has become inactive by contacting the immobilizate containing the inactive enzyme with a solution of inorganic ammonium sulfate or a solution of primary, secondary, tertiary or quaternary $C_1$ to $C_6$ alkyl or hydroxy alkyl ammonium sulfate to desorb the enzyme and then contacting the support with a fresh enzyme solution to adsorb active enzyme to the support.

6 Claims, No Drawings

REGENERATION OF AN ENZYME IMMOBILIZATE

CROSS REFERENCE TO RELATED APPLICATION

This application is related to Copending U.S. patent application Ser. No. 957,519 of Nov. 3, 1978, directed to a method of immobilizing enzymes on an inorganic support material and the use of the enzyme immobilizate for the selective enzymatic saponification of N-acyl amino acids of Messrs. Franzmann and Hülsmann, assigned to the assignee hereof.

BACKGROUND OF THE INVENTION

1. Field of the Invention

This invention relates to regeneration of enzyme immobilizates such as enzyme-containing catalyst composition comprising a solid support and an enzyme disposed thereon. More especially, this invention relates to the regeneration of such enzyme immobilizates by a simple and gentle method of desorbing the inactivated enzyme thereon, permitting the preparation of a rejuvenated enzyme immobilizate by contacting the so-treated enzyme immobilizate with solution containing fresh enzyme. More especially, this invention is directed to a method for removing inactivated enzyme from an enzyme immobilizate containing inactivated enzyme.

2. Discussion of the Prior Art

The regeneration of enzyme immobilizates either is not feasible or, in accordance with the prior art, has to be effected under very drastic conditions. According to German patent application DAS No. 25 37 671, a pyrolysis is carried out at temperatures ranging from 500° to 900° C. According to German patent application DOS No. 27 20 538, regeneration is effected with aqueous mineral acid and alkali lye in the case of a glucose isomerase immobilized in organic ion-exchange resin.

These methods merely result in the recovery of the support free of enzyme. And frequently they will result in damage to active enzyme which is still bound, and also to the support, especially when a modifier has been applied to the latter with which the enzyme is spatially associated in the immobilizate.

There has been a need for a method of regeneration of enzyme immobilizates whose activity has been reduced through damage to the enzyme which method is not only simple, but also gentle, at least which respect to the support, including its enzyme-binding functions.

SUMMARY OF THE INVENTION

It is an object of this invention, therefore, to provide a simple but gentle means for the removal of damaged or inactive enzymes from an enzyme immobilizate which method does not damage the support or adversely affect any enzyme-binding ability of the support. More especially, this invention is directed to a simple means for the removal of inactive or damaged enzymes from solid enzyme immobilizates comprising an enzyme physically adsorbed to a solid siliceous support containing an amino alkoxy silane, the composition being free of unabsorbed enzyme. It is a further object of this invention to provide a process for the removal of damaged or inactivated enzymes such as N-acyl-L-amino acid amidohydrolase from enzyme immobilizates comprising a solid siliceous support and an amino alkoxy silane in addition to said enzyme.

In accordance with this invention, inactive or damaged enzyme is removed from an enzyme immobilizate by desorption. Desorption in accordance with the present invention can be carried out by contacting the immobilizate containing the inactivated enzyme with a salt solution. After the inactivated enzyme has been desorbed from the immobilizate, the support can be regenerated by contacting the same with a fresh enzyme solution.

A wide variety of salt solutions are useful for this purpose, including in particular aqueous salt solutions. However, polar organic solvents can be used, provided they are sufficiently polar that the salt is soluble therein. Particularly contemplated solutions of polar organic solvents include alcoholic salt solutions. Additionally, one can employ a mixture of a polar solvent and water as the solvent for the salt. In any event, it is preferred that the salt solution have a neutral or weakly alkaline pH value in the range of 5 to 11, preferably 7 to 9. Highly preferred are buffered salt solutions. Ammonium sulfate solutions have proven particularly advantageous. However, solutions of sodium acetate and optionally, primary, secondary, tertiary or quaternary $C_1$ to $C_6$ alkyl ammonium sulfate solutions can also be used singly or in combination with any other useful salt.

The salts to be used in the form of an aqueous or polar organic solvent solution include: e.g. monomethyl to tetra methyl ammonium sulfate, mono ethyl to tetra ethyl ammonium sulfate, the correspondic mono to tetra propyl and butyl ammonium sulfates, alkyl ammonium sulfates with mixed alkyl groups as N-methyl-N-ethyl ammonium sulfate or N,N-dimethyl-N-ethyl ammonium sulfate, and the corresponding hydroxy alkyl ammonium sulfates of $C_1$ to $C_6$ alkyls as hydroxy ethyl ammonium sulfate, tri-hydroxy ethyl ammonium sulfate or hydroxybutyl ammonium sulfate.

The concentration of the salts in the solution will usually be comprised between 10 and 40 weight percent and is preferably comprised between 20 and 30 weight percent.

The temperature of regeneration is in the same range as that in which the enzymes are applied to the support and in which the enzyme immobilizates are utilized, that is to say, usually between 0° and 60° C., and preferably between 20° and 40° C.

Desorption and reactivation generally require not more than from 10 to 24 hours. Both desorption and reactivation with the enzyme solution are usually effected by allowing the solutions to stand, or by passing them through the immobilizate to be regenerated, the latter being maintained either stationary or in slight motion.

Generally speaking, an amount of wash or buffer solution is employed corresponding to between 5 and 100, preferably between 10 and 30 cc per gram of immobilizate being treated.

It is surprising that upon regeneration a complete enzyme immobilizate is obtained and that the method may be carried out under mild conditions resembling those under which the immobilizates are prepared and utilized.

After washing with these desorption solutions, the support can be washed with conventional dilute buffer solutions (such as acetic acid/acetate buffer, phosphate buffer; pH about 7 to 9) and concentrated with a fresh enzyme solution whereby it is reactivated.

The method in accordance with the invention is suited for enzyme immobilizates in which the enzyme is not covalently bound to the support but is held to it by ionic attraction or adsorption, for example.

Such enzyme immobilizates may be of widely differing nature. However, they are, in particular, enzyme immobilizates prepared in accordance with copending U.S. patent application Ser. No. 957,519, the disclosure of which is hereby specifically incorporated herein by reference, which alkoxy silanes containing amino alkyl or amino aryl groups are applied to inorganic supports, and particularly to such supports containing $SiO_2$, and the enzyme is associated with said silanes but is not covalently bound to them.

In accordance with U.S. Ser. No. 957,519, novel enzyme immobilizates are prepared in which the enzyme is physically adsorbed to a solid siliceous support containing an amino alkoxy silane. The composition is substantially free of unabsorbed enzyme. The novel enzyme immobilizate can be prepared by contacting a siliceous support comprising amorphous silica, prior to contact with the enzyme, with an alkoxy silane containing one or more amino groups. As the next step, the so-pretreated siliceous support is contacted with the enzyme. There is formed a novel enzyme composition wherein the enzyme is not covalently bonded to the support and/or the amino alkoxy silane. Useful silanes for this purpose includes silanes of the formula

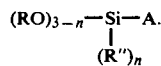

The silanes falling within the formula include the following alkoxy silanes:

γ-aminopropyltrimethoxysilane, γ-aminopropyltriethoxysilane, β-aminoethyl-trimethoxysilane, N-aminoethyl-γ-aminopropyltriethoxysilane, N-aminoethyl-γ-aminopropyltrimethoxysilane, p-aminophenyltriethoxysilane, γ-dimethylaminopropyltrimethoxysilane, γ-dimethylaminopropyl-triethoxysilane, γ-methyl-γ(β-aminoethyl)-aminopropyltrimethoxysilane, γ-methyl-γ(β-aminoethyl)-aminopropyl-triethoxysilane, γ-ethylaminopropyl-trimethoxysilane, γ-methylaminopropyltrimethoxysilane, γ-dimethylaminopropyl-methyl-dimethoxysilane, γ-dimethylaminopropyl-phenyl-dimethoxysilane, γ-(β-dimethylaminoethyl)-aminopropyl-trimethoxysilane, or γ-(β-dimethylaminopropyl)-aminopropyl-trimethoxysilane, or γ-(1,3-diazacyclopentyl-2)-propyl-trimethoxysilane.

Enzymes which can be employed in such a system include N-acyl-L-amino acid amidohydrolases, called briefly aminoacylases or acylases, which in acylated mixtures of D, L-amino acids selectively deacylate the L form to the L-amino acid. The acyl groups in the substrate can be of any kind, but acetyl groups are preferred. The acylases are obtained from animal organs such as pig kidneys or cattle pancreases or from special strains of micro-organisms such as Aspergillus oryzae (AMANO acylase) in the form of water-soluble proteins.

A combination of the method of regeneration of enzyme immobilizates in accordance with the invention with the method of enzyme immobilization on an organic support in accordance with U.S. Ser. No. 957,519 offers the special advantages of immobilization of enzymes on supports in which through special measures the enzymes are not covalently bound to the support treated with silanes but are permanently associated with it in an apparently spatial arrangement.

When the loss of activity of an enzyme immobilizate is due, not to impairment of the immobilized enzyme but merely to an enzyme loss attributable to slow desorption after prolonged use, reactivation with fresh enzyme solution which may be preceded by brief washing with dilute buffer solution in place of washing with desorption solution will suffice. Such dilute buffer solutions will usually contain from 1 to 10 weight percent of the buffer substances and have a pH value within the range indicated.

In order to more fully illustrate the nature of the invention and the manner of practicing the same, the following examples are presented:

EXAMPLE 1

8 g (moist weight) of an enzyme immobilizate prepared by incubation of 5 g of a porous $SiO_2$ with γ-aminopropyltriethoxysilane followed by application of an AMANO acylase solution (in accordance with U.S. patent application Ser. No. 957,519) was treated at 37° C. three times every 8 hours with 30 ml each of a 20 wt. % aqueous ammonium sulfate solution of pH 7. The immobilizate was washed for 20 min. with 30 ml of a 2 wt. % acetate buffer of pH 7. After desorption, the activity, measured on the basis of the enzymatic hydrolysis of sodium-N-acetyl-DL-phenylalanine, was found to be from one-third to one-fourth of the original activity. The immobilizate was reactivated by incubation for 24 hours with 8 ml of a 10 wt. % AMANO acylase solution in acetate buffer at 22° C.

After washing with acetate buffer for removal of unbound enzyme, the immobilizate exhibited, also in longterm tests, the same activity as the original immobilizate.

The tests were conducted at 20° C. and at 45° C. with the same results.

In place of 20 wt. % ammonium sulfate solution, 30 and 40 wt. % ammonium sulfate solutions have been used with the same results.

EXAMPLE 2

Example 1 was repeated with corresponding immobilizates in which the immobilized enzyme had been impaired through (a) an excessively high operating temperature (over 50° C.), (b) contaminated substrate solutions (containing, for example, complexing agents such as thiols or cadmium), and (c) excessively high substrate concentrations of over 25 wt. % sodium-N-acetylphenylalanine. After the regeneration steps had been carried out, immobilizates were obtained whose activity was on a par with that of preparations freshly made in accordance with U.S. patent application Ser. No. 957,519.

EXAMPLE 3

Example 1 was applied with corresponding amounts of solution to the enzyme immobilizate of a column charge which originally had been prepared in accordance with U.S. application Ser. No. 957,519 from 250 g of a porous $SiO_2$ support with γ-aminopropyltrialkoxysilane and an acylase and which after 60 days' use in the preparation of L-phenylalanine from sodium-N-acetyl-DL-phenylalanine exhibited about 55% of its initial activity. After regeneration in accordance with Example 1, the column charge was found to have an activity about 10% higher than the original activity.

EXAMPLE 4

Example 3 was carried out on a column charge which after 90 days' use in the preparation of L-tryptophan from sodium-N-acetyl-DL-tryptophan had about 35% of its original activity. After regeneration, the column charge was found to have about 90% of its original activity.

EXAMPLE 5

Example 3 was carried out with one-half of a column charge which after 100 days' use in the preparation of L-phenylalinine from sodium-N-acetyl-DL-phenylalanine had about 25% of its initial activity. Regeneration restored the column charge to its initial activity.

EXAMPLE 6

The other half of the column charge mentioned in Example 5 was regenerated without the use of a salt solution by washing with a 2 wt. % acetic acid/sodium acetate buffer solution and treatment with acylase solution. The catalyst (enzyme) then was found to have about 80% of its original activity.

EXAMPLE 7

Example 1 was repeated with enzyme immobilizates which had been prepared from an $SiO_2$ support and p-aminophenyltrimethoxysilane and acylase and whose activity had been reduced in use to about 40 to 60% of the original level. They then exhibited an activity equal to 95 to 100% of their original activity, which was sustained in continued similar use for as long as that of freshly prepared enzyme immobilizates.

EXAMPLE 8

Example 1 was repeated, in place of ammonium sulfate, an aqueous ethylammonium sulfate solution of 25 wt. % has been used with the same results.

EXAMPLE 9

Example 1 was repeated, in place of ammonium sulfate, an aqueous trimethylammonium sulfate solution of 25 wt. % has been used with the same results.

EXAMPLE 10

Example 8 was repeated, in place of water, a mixture of ethanol and water (2:8 volume parts) was used to prepare the desorption solution.

EXAMPLE 11

Example 1 was repeated, in place of ammonium sulfate, hydroxyethylammonium sulfate solution of 28 wt. % has been used with the same results.

We claim:

1. A method for regeneration of an enzyme immobilizate comprising an amorphous silicecous support to which there is bonded by adsorption via an amino alkoxy silane containing an amino alkyl or amino aryl group an inactivated enzyme which comprises desorbing said inactivated enzyme from said immobilizate by contacting said immobilizate with a solution of inorganic ammonium sulfate or a primary, secondary, tertiary or quaternary $C_1$ to $C_6$ alkyl or hydroxy alkyl ammonium sulfate having a concentration of 10 to 40 weight percent and a pH in the range of 5 to 11 and thereafter reactivating the so-treated immobilizate by conctacting the same with fresh enzyme solution to adsorb fresh enzyme to said support.

2. A method according to claim 1 wherein the salt solution has a pH in the range of 7 to 9.

3. A method according to claim 1 wherein the concentration of said ammonium sulfate solution is 20 to 30 weight percent.

4. A method according to claim 1 wherein the enzyme of the immobilizate is an acylase.

5. A method according to claim 1 wherein said solution is a solution of said primary, secondary, tertiary, or quaternary $C_1$–$C_6$ alkyl ammonium sulfate.

6. A method according to claim 1, wherein said inactivated enzyme is removed from said immobilizate by contacting said immobilizate with said solution of inorganic ammonium sulfate.

* * * * *